United States Patent [19]

Olson et al.

[11] Patent Number: 5,041,654

[45] Date of Patent: Aug. 20, 1991

[54] PREPARATION OF MONOSUBSTITUTED DITHIOOXAMIDE COMPOUNDS

[75] Inventors: David B. Olson, St. Croix; Robert J. Lokken, Maplewood; Roger A. Mader, Stillwater; Jacqueline M. Furlong, Oakdale, all of Minn.

[73] Assignee: Minnesota Mining and Manufacturing Company, St. Paul, Minn.

[21] Appl. No.: 438,765

[22] Filed: Nov. 17, 1989

[51] Int. Cl.$^5$ .................. C07C 327/42; C07C 327/44
[52] U.S. Cl. ................................... 564/77; 260/404.5
[58] Field of Search ........................ 564/77; 260/404.5

[56] References Cited

U.S. PATENT DOCUMENTS

| 3,252,910 | 5/1966 | Oberright | 252/42.7 |
|---|---|---|---|
| 3,318,675 | 5/1967 | Olin | 71/2.3 |
| 3,437,677 | 4/1969 | Bertsch et al. | 260/429 |
| 3,516,846 | 6/1970 | Matson | 117/36.2 |
| 3,658,900 | 4/1972 | Alt | 260/551 S |

FOREIGN PATENT DOCUMENTS

| 0548341 | 11/1957 | Canada . |
| 2246025 | 3/1974 | Fed. Rep. of Germany . |
| 0112435 | 4/1975 | German Democratic Rep. . |
| 0808425 | 2/1959 | United Kingdom . |

OTHER PUBLICATIONS

Persson et al., "Electronic Spectra of Thioamides and Thiohydrazides", *J. Acta. Chem. Scand.*, 18, 1059 (1964).

Haske et al., "Preparation of Unsymmetrical Dithiooxamides", *J. Org. Chem.* 32, 1579 (1967).

Hurd, *Review of the Scientific and Patent Literature on Dithiooxamide, its N-Substituted Derivatives and Their Metal Complexes*, Mallinkrodt Chemical Works, St. Louis, MO, 1963.

R. N. Hurd et al., *J. Am. Chem. Soc.*, 82, 4454 (1960).

A. D. Grabenko et al., *Zhur. Obshch. Khim.*, 30, 1222 (1960).

R. N. Hurd et al., *J. Org. Chem.*, 26, 3980 (1961).

A. D. Grabenko et al., *Zhur. Obshch. Khim.*, 31, 2739 (1961).

A. D. Grabenko et al., *Zhur. Org. Khim.*, 8, 528 (1972).

H. U. Kibbel et al., *J. Prakt. Chem.*, 323, 41 (1981).

*Chem. Abstr.*, 68, 39331n (1968), [JP 15925, (1967)].

*Primary Examiner*—Glennon H. Hollrah
*Assistant Examiner*—Peter G. O'Sullivan
*Attorney, Agent, or Firm*—Merchant, Gould, Smith, Edell, Welter & Schmidt, P.A.

[57] ABSTRACT

This invention relates to the synthesis of N-(monosubstituted)dithiooxamides by the transamination of dithiooxamide. Preferred methods, according to the present invention, take advantage of the discovery that yields of N-(monosubstituted)dithiooxamides can be improved in the Wallach Reaction by: controlling the temperature of the reaction mixture; optimizing the initial concentration of the reactants; adding an effective amount of acid in the quenching or processing procedure; and/or, optionally, adding an effective amount of certain nitrogen bases to the reaction mixture.

23 Claims, No Drawings

PREPARATION OF MONOSUBSTITUTED DITHIOOXAMIDE COMPOUNDS

FIELD OF THE INVENTION

The present invention concerns methods of organic synthesis, and in particular methods for the preparation of monosubstituted dithiooxamide compounds. More specifically, the invention concerns methods for preparing and isolating N-(monosubstituted)dithiooxamides.

BACKGROUND OF THE INVENTION

Dithiooxamide ($C_2H_4S_2N_2$) is a well-known and widely studied material of the structural formula I, as follows:

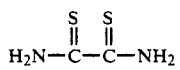

Dithiooxamide is also a well-known ligand for complexation or coordination with transition metal cations. In particular, it is known to coordinate with such cations as $Ni^{+2}$, $Zn^{+2}$, $Pd^{+2}$, $Pt^{+2}$, $Fe^{+2}$, $Cu^{30\ 2}$, and $Co^{+2}$.

Certain substituted dithiooxamides are also fairly well-known and widely studied. These are certain N,N'-(disubstituted)dithiooxamides according to the general formula II as follows:

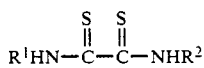

wherein $R^1$ and $R^2$ are a variety of alkyl or aryl groups, including straight chain or branched structures, and chains including heteroatoms therein, such as oxygen, nitrogen, or sulfur.

N,N'-(disubstituted)dithiooxamides, i.e., compounds according to formula II, are theoretically capable of forming a variety of types of complexes with transition metal cations. Three of these will be referred to herein as a "monomer" complex, a "cationic" complex, and a "polymer" complex represented by the formulas III, IV, and V, respectively.

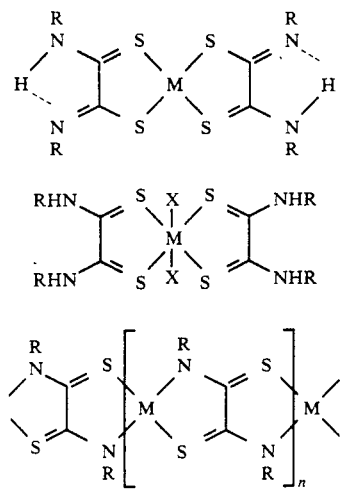

The monomer complex can be generally represented by the formula $M(HL)_2$ wherein M is a transition metal cation having an oxidation state of $+2$ and HL is a dithiooxamide ligand according to the general formula II, having an overall charge of $-1$ due to removal of one thioamide hydrogen therefrom.

The polymer complex comprises a one to one coordination between ligand and transition metal cation and can be generally characterized by the formula $(ML)_n$ wherein M is a transition metal cation having an oxidation state of $+2$ and L is a dithiooxamide ligand according to formula II, wherein two thioamide hydrogens (one from each nitrogen) have been removed resulting in an overall charge on the ligand of $-2$.

The "cationic" complex is represented by the general formula $M(H_2L)_2X_2$ wherein M is a transition metal cation having an oxidation state of $+2$, $H_2L$ is a dithiooxamide ligand generally represented by formula II above, and X is an anion having a charge or valence number of $-1$.

Formulas III, IV, and V are for the purpose of representing stoichiometry only. The coordination of the ligands may vary, thus allowing for a variety of isomers.

The polymer complexes of N, N'-(disubstituted)dithiooxamides are known and have been studied. In part, this is due to the fact that they exhibit a strong, typically magenta, color. As a result, they have been commercially used in products such as carbonless paper constructions.

Generally, a carbonless paper construction comprises two substrates, for example two sheets of paper, each with one face, or side, coated with a reactant. The two substrates are generally referred to as a donor sheet and a receptor sheet. When the coated faces of the two substrates come into contact such that the reactants can mix, a reaction occurs and an image forms.

In a typical carbonless transfer paper construction, the donor sheet generally includes thereon a coating of encapsulated ligand material in a suitable binder, and is often referred to as the coated back (CB) sheet. The receptor sheet generally includes a coating of a transition metal salt optionally in a suitable binder, and is often referred to as the coated front (CF) sheet. The metal salt is such that it is capable of forming the polymer when brought into contact with the dithiooxamide ligand. In use, the donor sheet and receptor sheet are placed with the CB surface in contact with the CF surface. That is, the two sheets are positioned such that the capsule coated donor (CB) sheet faces the metal salt coating on the receptor (CF) sheet. Stylus pressure (for example pen pressure) or key pressure (for example typewriter key pressure) applied to a frontside of the donor sheet, i.e., the uncoated face, will tend to break the capsules containing the ligand, releasing same to transfer to the surface of the receptor sheet and form a colored complex with the metal salt thereon. With respect to this, attention is directed to G. W. Matson, U.S. Pat. No. 3,516,846 (1970). The appropriate stylus or key pressure will be generally referred to herein as "activating pressure." Such systems are generally referred to as "carbonless paper" arrangements, since a copy of what is printed or typed onto the donor sheet is generated on the receptor sheet without benefit of carbon paper.

As explained above, generally N, N'-(disubstituted)-dithiooxamides form magenta polymer complexes with nickel. This is less than ideal for carbonless paper products, since darker blue or blue-black colors are preferred for both aesthetics and contrast. Therefore, alternatives to N,N'(disubstituted)dithiooxamides have been sought as ligands for use in such products or for use in any applications in which a blue image is desirable.

It has recently been discovered that certain N-(monosubstituted)dithiooxamides react with transition metal cations to form dark, i.e., blue or blue-black, colored polymer complexes. With respect to this, see copending U.S. application Ser. No. 07/438,776. It is noted that mixtures of both N-(monosubstituted)dithiooxamides and N,N'-(disubstituted)dithiooxamides may be useful for carbonless paper.

The present application concerns preferred methods for the synthesis and isolation of N-(monosubstituted)-dithiooxamides. As will be apparent from the following descriptions, conventional methods for synthesizing substituted dithiooxamides have not been completely acceptable for achieving this end.

The reaction of unsubstituted thioamides with primary aliphatic amines, known as the Wallach Reaction, has been used in the preparation of substituted dithiooxamides. See O. Wallach, *Ann.* 1891, 262, 324. In particular, a variety of N,N'-(disubstituted)dithiooxamides have been prepared by this method; see for example R. N. Hurd et al., *J. Org. Chem.* 1961, 26, 3980.

The Wallach Reaction is a transamination reaction. It is limited in that aromatic primary amines, such as aniline, and secondary aliphatic amines, such as diethylamine or diethanol amine, are unreactive under the typical reaction conditions. Additionally, the Wallach Reaction generally favors formation of the symmetrically disubstituted product, and monosubstituted products are difficult to isolate in significant yields. See, for example, G. H. Alt, *U.S. Pat. No.* 3,658,900 (1972) and B. Persson et al., *Acta Chem. Scand.* 1964, 18, 1059.

A variation of the Wallach Reaction has been used to favor formation of N-(monosubstituted)dithiooxamide compounds. In particular, Haske et al., *J. Org. Chem.* 1967, 32, 1579, have reported preparation of several aliphatic-substituted dithiooxamides according to a one-step synthesis that makes use of the acidic nature of the thiooxamide proton. In general, Haske et al. proceeded through blocking one of the thioamide functions, by formation of the dithiooxamide salt. Reaction of the salt with an aliphatic amine was reported to give a low yield of monosubstituted dithiooxamide. Via their process, they reported the preparation of N-ethyl, N-propyl, N-butyl, N-3dimethylaminopropyl, N-2-hydroxyethyl, and N-3-hydroxypropyl derivatives of dithiooxamide. Typically, yields ranged from about 5.7% (for the N-butyl compound) to 15.3% (for the hydroxyethyl compound). The reactions, which were carried out in aqueous sodium hydroxide, were typically accompanied by hydrolytic decomposition of the dithiooxamide, leading to formation of ammonia, sulfide, cyanide, thiocyanate, and oxalate ions. Attempts to minimize hydrolysis by shorter reaction times typically resulted in increased recovery of starting material.

Alternative methods for preparing N-(monosubstituted)dithiooxamide derivatives are known. For example, see H. U. Kibbel et al., *J. Prakt. Chem.* 1981, 323, 41, and G. Erfurt et al., *D. D. R. Patentschrift* 112,435 (1975). This synthesis is based on reacting sodium cyanodithioformate with an amine, followed by treatment with hydrogen sulfide to form a dithiooxamide. The toxicity of hydrogen sulfide, the handling and filtering of cyanide solutions, as well as the flammability of carbon disulfide used in this reaction, serve to make the reaction undesirable for use in large-scale production for commercially useful monosubstituted dithiooxamides.

Other routes for the preparation of monosubstituted dithiooxamides include the use of various toxic and hazardous materials, which create the same problems as mentioned above with respect to commercial production. For example, phosphorus pentasulfide has been used in the treatment of N-phenyloxamide to prepare N-phenyldithiooxamide; see A. Reissert, *Chem. Ber.* 1904, 37, 3708. Also, isothiocyanates have been used in reaction with potassium cyanide, the product of which was then reacted with ammonia and hydrogen sulfide to form various N-(monophenyl)dithiooxamides. See A. Reissert, *Chem. Ber.* 1924, 57B, 981 and A. D. Grabenko et al., *Zh. Org. Khim.* 1972, 8, 528.

It is noted that the methods reported above, specifically developed to favor preparation of monosubstituted dithiooxamides, have only been used to prepare compounds substituted with relatively short-chain alkyl groups or aryl groups with short-chain substituents. That is, methods for the preparation of N-(monosubstituted)dithiooxamides, wherein the groups substituted on the nitrogen are sufficiently large to render substantial nonvolatility in the monosubstituted product, and thus potential useability in commercial applications such as carbonless paper products, have not been shown in the literature. The need for the preparation of such compounds exists due to the commercial utility of products with a blue or blue-black image.

It would be preferred that the methods of synthesis be such as to render: favorable, or at least commercially acceptable, overall yields of monosubstituted materials; favorable, or at least commercially acceptable, ratios between monosubstituted material and disubstituted material; product mixtures from which the desired monosubstituted material can be readily isolated; and, reaction conditions and reagents that are acceptable in large scale production runs. It will be seen from the following descriptions that the methods described herein advance these causes significantly.

SUMMARY OF THE INVENTION

This invention relates to the synthesis of N-(monosubstituted)dithiooxamides by the transamination of dithiooxamide. Preferred methods, according to the present invention, take advantage of the discovery that yields of N-(monosubstituted)dithiooxamides can be improved in the Wallach Reaction by: controlling the temperature of the reaction mixture; optimizing the initial concentrations of the reactants; adding an effective amount of acid to benefit the work-up, i.e., processing, procedure; and/or, optionally, adding an effective amount of certain nitrogen bases to the reaction mixture. Herein, an "effective amount" of a material means a sufficient amount to result in any of the following: a relative increase in yield of the monosubstituted dithiooxamide derivative; a relative increase in the ratio of the yields of the mono- to the disubstituted derivatives; a relative decrease in the amount of dithiooxamide starting material needed; or, an improvement, or simplification, in the processing procedures, i.e., purification and isolation. An "improved" procedure is one similarly defined.

The base that is optionally added for the purpose of enhancing the formation of the monosubstituted dithiooxamide, herein referred to as the "auxiliary" or "nonreactive" base, must itself generally not react with the dithiooxamide in the same manner as the amine that undergoes the transamination reaction, herein referred to as the "reacting" or "reactive" base. In some circumstances, the typical bases that are effective in promoting enhanced yields of monosubstituted dithiooxamides are nitrogen bases including: aromatic primary amines; secondary and tertiary aliphatic amines; aromatic heterocyclic compounds; and mixtures thereof. Examples of these nitrogen bases are aniline, diethylamine, pyridine, and mixtures thereof.

In general, reactions according to the present invention are conducted between dithiooxamide itself (rather than a deprotonated form, as would be present if the reaction were conducted in the presence of a strong hydroxide base), and the reactive amine, in solution. It will, therefore, be preferable that the nonreactive base be a relatively weak base.

Compounds synthesized by this improved method are useful in the preparation of coordination compounds with transition metal cations. Certain of these monosubstituted ligands form complexes that are useful in image formation by pressure sensitive imaging techniques, because of their desirable colors and physical properties.

DETAILED DESCRIPTION OF THE INVENTION

As required, detailed descriptions of the present invention are provided herein. In general, the detailed descriptions are to be considered as exemplary only.

The synthesis of dithiooxamide derivatives by the Wallach Reaction consists of reacting an amine with dithiooxamide in a solvent, such as alcohol. In conventional procedures, when an initial 1:1 molar ratio of amine to dithiooxamide is used, the monosubstituted and disubstituted derivatives are typically formed in about the same amounts; see B. Persson et al., *Acta Chem. Scand.* 1964, 18, 1059. Persson et al. report, for example, N-methyldithiooxamide in 19% yield, and N,N'-dimethyldithiooxamide in 13% yield from a reaction of an equimolar ratio of methylamine and dithiooxamide in alcohol.

In preferred applications of the present invention, the temperature and concentration of the reactants in the Wallach Reaction mixture are controlled and the reaction is quenched with acid. Optionally, an auxiliary base is provided in the Wallach Reaction mixture. The described control of the temperature, concentration of reactants, acid quenching, and the optional use of the proper auxiliary base favor N-(monosubstituted)dithiooxamide formation, isolation, and/or yield.

The Auxiliary Base

As indicated above, the formation of N-(monosubstituted)dithiooxamide compounds via the Wallach Reaction, i.e., transamination involving reaction of dithiooxamide with an amine, is for certain reactions favored by the presence of an auxiliary base. In general, auxiliary bases useable to achieve the desired effect are nitrogen bases, i.e., amine bases, generally unreactive under the conditions of the Wallach Reaction. These bases include aromatic primary amines, secondary and tertiary aliphatic amines, and aromatic nitrogen-containing heterocyclics, i.e., aromatic compounds containing nitrogen in at least one of the aromatic rings, and mixtures thereof. Preferred such bases include pyridine, aniline, diethylamine, and mixtures thereof.

When a nonreactive auxiliary base is used, preferably about 0.5 to 3.0 molar equivalents of the auxiliary base, relative to dithiooxamide, is initially used. Most preferably, the initial molar ratio of nonreactive auxiliary base to dithiooxamide is within the range of about 0.5 to 1.2.

It will be seen from results presented herein below, in Table II, that the optimum conditions for this reaction generally involve the initial use of an approximate equimolar ratio of nonreactive base to the dithiooxamide. This results in an enhancement in the yield of the monosubstituted derivative relative to the disubstituted derivative of dithiooxamide.

Positive effect on the yield of N-(monosubstituted)dithiooxamides, due to the use of an auxiliary base, is generally noted for reactions in which the reactive amine, $H_2NR'$, contains an alkyl or aralkyl group as the R' substituent. Herein "alkyl group" includes hydrocarbon groups consisting of straight chains, branched chains, cyclic structures, saturated groups, and unsaturated groups. These groups may also include various functional groups. The term "functional group" refers to groups involving heteroatoms substituted onto the alkyl group. Such functional groups include within their scope, but are not limited to, hydroxyl and halide groups. Positive effect is also noted for reactions in which the R' substituent on the reactive amine contains an amide linkage.

The positive effects of the presence of the nonreactive base in the formation of N-(monoalkylated)dithiooxamides are readily observable from the data reported below in Table I. In general, Table I is a comparison of two Wallach Reactions involving a transamination between hydroxyethylamine (HEA), i.e., ethanolamine, and dithiooxamide (DTO). The isolated products of interest are the monosubstituted product, N-(2-hydroxyethyl)dithiooxamide (MHE), and the disubstituted product, N,N'-di(2-hydroxyethyl)dithiooxamide (DHE). In both instances the reaction conditions are generally as described in Experiment 2 below, with the only significant difference being the presence or absence of the auxiliary base (pyridine). The reaction products were isolated by evaporation of the solvent and separation of the reaction mixture using column chromatography on silica gel as described in Experiment 2.

Note that for the percentage yields presented in the following tables, the theoretical yields were calculated for the two products as if each were the only product formed, with no competing reactions taking place. For the reactions specifically reported in the tables, the initial ratio of dithiooxamide to the reactive amine was about 1:1. Therefore, theoretical yield of the monosubstituted product is based on either reactant being the limiting reagent, since the stoichiometry involves 1 mole of reactive amine to 1 mole of dithiooxamide. For the disubstituted product, the theoretical yield is based on the reactive amine being the limiting reagent since the stoichiometry involves 2 moles of reactive amine to 1 mole of dithiooxamide. Note also that the mono:di ratios in all cases are molar ratios of the monosubstituted product to the disubstituted product of each reaction mixture.

TABLE I

| | | | | | | | |
|---|---|---|---|---|---|---|---|
| Effect of Base on Yield of Hydroxyethyl Dithiooxamides | | | | | | | |
| Amounts of Reactants | | | Amounts of Products | | % Yield | | Mono:Di |
| DTO | HEA | Pyridine | MHE | DHE | MHE | DHE | Ratio |
| 2.4 g<br>0.02 mol | 1.2 g<br>0.02 mol | — | 0.8 g<br>0.005 mol | 0.8 g<br>0.004 mol | 25% | 38% | 1.3:1 |
| 2.4 g<br>0.02 mol | 1.2 g<br>0.02 mol | 1.6 g<br>0.02 mol | 1.1 g<br>0.007 mol | 0.8 g<br>0.004 mol | 34% | 38% | 1.8:1 |

A variety of auxiliary bases may be used according to the present invention to promote reaction that results in increased yields of monosubstituted dithiooxamides. Table II shows the effects of different auxiliary bases and the effect of concentration of base on the yield of N-dodecyldithiooxamide relative to N,N'-didodecyldithiooxamide.

It can be seen from these results that the optimum amount of auxiliary base is generally an amount about equal to the number of moles of dithiooxamide. Note, however, that for this amount of base to be most effective, the concentration of the dithiooxamide should generally be within a preferred range, as described below.

For the data presented in Table II, the reactions were carried out generally as described in Experiment 1 below. The molar ratio between dithiooxamide and dodecylamine in each case was initially 1:1, and the concentrations of dithiooxamide and auxiliary base were varied according to the relative amounts listed.

TABLE II

| | | | | | |
|---|---|---|---|---|---|
| Effect of Base and Base Concentration on Yield of N-Dodecyldithiooxamide and N,N'-Didodecyldithiooxamide | | | | | |
| Auxil.<br>Base | Equiv<br>of Base | Wt %<br>DTO | Yield<br>Dodecyl-DTO | Yield<br>Didodecyl-DTO | Mono:Di<br>Ratio |
| none | 0 | 7 | 2.6 g (45%) | 2.1 g (46%) | 2.0:1 |
| aniline | 0.5 | 7 | 2.7 g (46%) | 2.3 g (50%) | 1.9:1 |
| aniline | 1 | 7 | 3.2 g (55%) | 1.5 g (33%) | 3.4:1 |
| aniline | 3 | 7 | 2.5 g (43%) | 2.1 g (46%) | 1.9:1 |
| aniline | 1 | 14 | 2.1 g (37%) | 2.7 g (60%) | 1.2:1 |
| pyridine | 1 | 7 | 2.3 g (41%) | 1.3 g (28%) | 2.9:1 |
| pyridine | 1 | 14 | 2.1 g (37%) | 2.3 g (50%) | 1.5:1 |

Reaction Conditions Favoring the N-(Monosubstituted) Product

Typical reaction conditions, for maximizing preparation of monosubstituted material according to the present invention, involve utilization of about a 0.8:1 to 3:1 molar ratio of dithiooxamide to reactive amine, preferably a 1:1 to 2:1 molar ratio, initially in the reaction solution. The use of an excess of dithiooxamide relative to the amount of reactive amine has been found to increase the mono- to di- substituted ratio, particularly for reactions in which an auxiliary base is not used.

For generally all substituents, a dilute reaction mixture favors formation of the monosubstituted product. In particular, when the reactants are initially used in a ratio of dithiooxamide to reactive amine of between about 0.8:1 and 3:1, preferably the concentration of DTO in the reaction solution is initially no greater than about 15% based on weight, and more preferably no greater than about 10%. Also, preferably the concentration of reactive base is initially no greater than about 15% by weight, and more preferably no greater than about 10%.

The effect of concentration is apparent from an examination of the data in Table II above and Table III below. In general, the experiments that led to the generation of the data of Table III were conducted according to the procedure outlined in Experiment 1 reported herein below, except for the variation of weight-% of the solvent in the reaction mixture. It is noted that for all reactions of Table III aniline was used as the auxiliary base to favor the formation of the monosubstituted product. In each reaction the weight-% of aniline used was in an amount that would generate about a molar equivalent of aniline to dithiooxamide.

Note that as the weight-% of the solvent increases, i.e., the concentrations of the reactants decrease, the molar ratio of the product yield of the monosubstituted derivative relative to the disubstituted derivative increases. Note also that although the yield of the monosubstituted derivative does not always increase substantially, if at all, the yield of the undesired disubstituted derivative generally decreases substantially. This is an improvement according to the present invention, since the ratio of monosubstituted product to disubstituted product is improved.

TABLE III

| | | | | |
|---|---|---|---|---|
| Effect of Concentration on the Formation of N-Dodecyldithiooxamide and N,N'-Didodecyldithiooxamide | | | | |
| Wt %<br>Solvent | Moles<br>DTO | Yield*<br>Dodecyl-DTO | Yield*<br>Didodecyl-DTO | Mono:Di<br>Ratio |
| 65 | 0.040 | 3.7 g (0.013 mol) | 5.5 g (0.012 mol) | 1.1:1 |
| 73 | 0.029 | 2.9 g (0.010 mol) | 2.9 g (0.0063 mol) | 1.6:1 |
| 80 | 0.020 | 2.4 g (0.0083 mol) | 1.5 g (0.0033 mol) | 2.5:1 |

*The dithiooxamide starting material used in these reactions was about 80% pure. The impurities were inert and, therefore, did not affect the reaction. As a result, the percentage yields appear deceptively low; however, the mono:di ratios were generally unaffected by the impurities.

It has also been observed that advantages are derived from maintaining a reaction temperature below the reflux temperatures of the solvent, and in particular preferably at 40° C. or below. With respect to this, attention is directed to the data reported in Table IV below.

The data of Table IV were generally developed from the experimental procedure outlined in Experiment 1, with the noted variations. Each experiment was conducted with 0.02 moles each of dithiooxamide and dodecylamine in methanol. In the two reactions where base is indicated to have been added, the auxiliary base was aniline, 0.02 moles of which was present. In the two reactions in which acid is indicated to have been added, 37% aqueous HCl was added after 3 hours of reaction time in an amount effective to adjust the pH of the solution to a value of about 2 to 5.

It is apparent from this data that temperature of reaction is a significant factor in improving the yield of the monosubstituted dithiooxamide compounds. Preferably, the temperature of the reaction mixture is maintained significantly below the reflux temperature of the solvent, which for methanol is 56° C. Most preferably, the temperature of the reaction is maintained between about 30° C. and 40° C. for optimum results.

TABLE IV

Effect of Temperature, Base, and Acid Quench on the Formation of N-Dodecyldithiooxamide and N,N'-Didodecyldithiooxamide

| T (°C.) | Time | Auxil. Base | Acid | Product Yields Dodecyl-DTO | Didodecyl-DTO | Mono:Di Ratio |
|---|---|---|---|---|---|---|
| 56 | 1 hr | *no | *no | 2.1 g (36%) | 1.0 g (22%) | 3.5:1 |
| 35 | 3 hr | no | no | 2.5 g (43%) | 1.8 g (39%) | 2.2:1 |
| 35 | 3 hr | no | **yes | 2.6 g (45%) | 2.1 g (46%) | 2.0:1 |
| 35 | 3 hr | **yes | no | 2.8 g (49%) | 1.1 g (24%) | 4.2:1 |
| 35 | 3 hr | yes | yes | 3.2 g (55%) | 1.5 g (32%) | 3.3:1 |

*no = the indicated reagent was not added to the reaction mixture (i.e., either no auxiliary base was used in the reaction, or no acid was used to quench the reaction).
**yes = the indicated reagent was added to the reaction mixture (i.e., if base, 0.02 moles of aniline was initially present in the reaction mixture; if acid, 37% aqueous HCl was added to quench the reaction and adjust the pH of the solution to a value of about 2 to 5).

It has also been determined that certain procedures for quenching the reaction can be utilized to improve the quality of the N-(monosubstituted)dithiooxamide product. In particular, the addition of acid to quench the reaction appears to improve product quality, as evidenced in part by the observed color of the reaction mixtures, which is a very pale color in reactions in which acid addition is employed. This tends to indicate that there are fewer undesirable side products from which the monosubstituted product must be separated.

Separation and isolation of the desired product is also improved by the addition of acid to quench the reaction, especially when the desired product includes a hydrophobic moiety therein. For example, in the preparation of N-(monoalkyl)dithiooxamides with long-chain substituents, such as those wherein the alkyl group is about 12 to 20 carbons, the N,N'-(dialkyl)dithiooxamide, which is formed as an undesirable side product, is observed to be relatively insoluble in the alcoholic reaction solvent after treatment with concentrated acid. However, the monosubstituted material is soluble, even after the acid addition. Thus, the disubstituted material is easily separated out by filtration, which facilitates the purification and isolation of the desired N-(monosubstituted)dithiooxamide product. In fact, the monosubstituted product can typically be isolated in a substantially pure, uncontaminated state by a subsequent precipitation, as for example with water. This is an improvement according to the present invention, since the isolation and purification procedures are simplified.

Further, the product yield of the monosubstituted derivative can in some situations be enhanced by the addition of acid to quench the reaction.

Typically, to quench the reaction, sufficient acid, such as 37% HCl, is added to the reaction solution to render a pH value of about 2 to 5. Acids that generally produce desirable results are strong mineral acids. Organic acids with approximately the same strength as mineral acids, as for example, trichloroacetic acid and trifluoromethanesulfonic acid, may also provide desirable results and are included within the scope of the invention. Acid addition is an advantageous aspect of the invention, it is believed, because the acid reduces the formation of side products by forming salts of any unreacted amine compounds.

As stated above, the color of the reaction product mixtures are distinctively lighter when acid is used to quench the transamination reactions. The significant impact of the use of acid on the quality of the product, however, is not readily quantified. Whether auxiliary base is used in the reaction or not, the addition of acid generally improves the purity and ease of isolation of the products. For example, when acid is not used, further reactions can occur during the processing procedure. The resulting product mixture can be an intractable oil. In many situations, the products are generally separated and purified using column chromatography. With acid addition, however, methods more amenable to scale-up of the procedure, such as extraction and precipitation, can be used. Therefore, certain methods of this invention significantly improve the synthesis of the monosubstituted dithiooxamides on a commercial scale.

The present invention will be further described by reference to the following detailed examples.

EXPERIMENTAL EXAMPLES

The following examples illustrate utilization of the improved methods reported herein, for preparation and isolation of N-(monosubstituted)dithiooxamide products. The procedures are particularly useful for preparation of preferred such products wherein the group substituted onto the dithiooxamide is such as generally renders the resulting product relatively nonvolatile. The data reported in Tables I–IV above, serve to support the general observations that:

(a) preparation of N-(monosubstituted)dithiooxamide compounds, in the Wallach transamination reaction, is generally favored by the presence of an auxiliary base, such as a nitrogen base not reactive under typical Wallach Reaction conditions;

(b) conduction of the reaction at temperatures below the reflux temperature of the solvent, and preferably within the range of about 30° C. to 40° C., generally favors formation of the monosubstituted product relative to the disubstituted product and minimization of undesirable side reactions;

(c) dilute reaction mixtures, wherein the ratio of the dithiooxamide to reactive amine is initially within the range of about 0.8:1 to about 3:1 and the concentration of dithiooxamide is preferably no greater than about 15%, and more preferably no greater than about 10%, generally favor formation of the monosubstituted product; and, (d) quenching of the reaction with acid favors isolation of the N (monosubstituted)dithiooxamide product in a manner that is amenable to commercial scale-up.

It is noted that the auxiliary base provides advantageous results in the formation of monoalkylated dithiooxamides. That is, positive effect on the yield of N-(monosubstituted)dithiooxamides, due to the use of an auxiliary base, is generally noted for reactions in which the reactive amine, $H_2NR'$, contains an alkyl or aralkyl group as the R' substituent. As stated previously, herein "alkyl group" includes hydrocarbon groups consisting of straight chains, branched chains, cyclic structures, saturated groups, and unsaturated groups. These groups may include various functional groups, i.e., groups involving heteroatoms substituted onto the alkyl group. Included within this definition are, without limitation, hydroxyl and halide groups.

Positive effect from the auxiliary base is also noted for reactions in which the R' substituent on the reactive amine, $H_2NR'$, contains an amide linkage. Positive effect is, for example, manifested by a reduction in the amount of dithiooxamide needed. Reduction in the amount of dithiooxamide required results in a cost-savings because dithiooxamide is a relatively expensive starting material. Also, isolation and separation procedures generally are simplified, when less dithiooxamide is used.

Certain classes of compounds, are indirectly synthesized to advantage by the presence of added auxiliary base in the Wallach Reaction. That is, a variety of compounds can be derivatized from a simpler monosubstituted dithiooxamide, which is synthesized to advantage by the method of the invention. For example, monosubstituted dithiooxamides wherein the substituent contains an ester group can be readily produced from the reaction of an acyl halide with a N-(hydroxyalkyl)dithiooxamide. The N-(hydroxyalkyl)dithiooxamide is readily synthesized by the reaction of dithiooxamide and a hydroxyalkylamine, and is facilitated by the presence of an auxiliary base.

EXPERIMENT 1

Preparation of N-Dodecyldithiooxamide

The data reported in Tables II, III, and IV were developed according to a procedure analogous to that reported herein for Experiment 1, with the variations noted in the tables.

Into a 100 ml round-bottomed flask, equipped with a magnetic stirrer, condenser, and heating bath, were placed 2.4 g (0.02 mol) of dithiooxamide, 1.8 g (0.02 mol) of aniline, and 40 ml of methanol. The solution was stirred and heated at 35° C. for 30 minutes. The reactive amine, dodecylamine (3.7 g, 0.02 mol), was then added, and the solution was stirred for an additional 3 hours at 35° C. The crude reaction mixture was cooled to 25° C., and the acidity was adjusted to a pH of about 2 by the addition of 37% HCl (aqueous). The precipitate that formed was collected by filtration, washed with a small amount of methanol, and dried to afford 1.5 g of a tan solid (product 1). Water (40 ml) was added to the filtrate with stirring, which was continued for 10 minutes. The precipitate was collected by filtration, washed with a minimum amount of a 50:50 mixture of water and methanol, and dried to afford 3.2 g of a brown solid (product 2).

A drop of product 1 dissolved in ethyl acetate was deposited on a TLC plate and eluted with a 50:50 mixture of ethyl acetate and hexane. It was observed that product 1 was essentially a single compound. A 2% nickel nitrate solution in a 50:50 mixture of ethanol and water was sprayed on the spot, which developed a magenta color characteristic of a nickel coordination compound with an N,N'-(dialkyl)dithiooxamide. Further, the product was identified by $^1H$ and $^{13}C$ NMR as being consistent with N,N'-didodecyldithiooxamide. The weight of the product was 1.5 g ($3.3 \times 10^{-3}$ mol), representing a 33% yield.

Product 2 was dissolved in ethyl acetate and a drop of the solution was deposited on a TLC plate. Elution with a 50:50 mixture of ethyl acetate and hexane was conducted. The product was observed to contain only one component, which developed a blue color when treated with a 2% solution of nickel nitrate and ethanol/water solvent. By $^1H$ and $^{13}C$ NMR, the product was identified as N-dodecyldithiooxamide. The yield corresponded to 0.011 mol, or 55% yield.

EXPERIMENT 2

Preparation of N-(2-Hydroxyethyl)dithiooxamide

The data of Table I was generally developed according to procedures analogous to those reported herein for Experiment 2.

Into a 100 ml round-bottomed flask, equipped with a magnetic stirrer, condenser, and heating bath, were placed 2.4 g (0.02 mol) of dithiooxamide and a solution of pyridine (1.6 g, 0.02 mol) dissolved in methanol (40 ml). The reaction mixture was heated, with stirring, at 35° C. for 30 minutes. Ethanolamine (1.2 g, 0.02 mol) was added, and the solution was stirred for an additional 3 hours at 35° C. The crude reaction mixture was cooled to room temperature, and the acidity was adjusted to a pH of about 2 by the addition of 37% HCl (aqueous). Silica gel (10 g) was added to the solution, and the solvent was removed under reduced pressure. The dry residue of silica gel with absorbed product mixture was added to a chromatography column. The products were eluted with an ethyl acetate/hexane mixture to separate the monosubstituted product, which was eluted first, from the disubstituted dithiooxamide. The yield of N-(2-hydroxyethyl)dithiooxamide was 1.1 g ($7.0 \times 10^{-3}$ mol, 34% yield). In addition, 0.8 g ($4.0 \times 10^{-3}$ mol, 38% yield) of N,N'-di(2-hydroxyethyl)dithiooxamide was isolated. The mole ratio of monosubstituted to disubstituted dithiooxamide was 1.8:1.

EXPERIMENT 3

Preparation of N-(2-Octanoyloxyethyl)dithiooxamide

The compound N-(2-hydroxyethyl)dithiooxamide, the preparation of which is described in Experiment 2, can be utilized as a precursor for the formation of a variety of higher molecular weight N-(monosubstituted)dithiooxamides. As previously described herein, such compounds are potentially commercially useful, as they generally form blue or blue-black complexes with certain transition metals, for example $Ni^{+2}$. They are also relatively nonvolatile and thus are more easily handled and are more readily useable in products such as carbonless paper constructions.

The present description of the synthesis of N-(2-octanoyloxyethyl)dithiooxamide is exemplary of the manner in which N-(2-hydroxyethyl)dithiooxamide can be used to prepare selected high molecular weight N-(monosubstituted)dithiooxamides.

Into a 250 ml round-bottomed flask, equipped with a rotary stirrer, condenser, and heating bath, were placed 6.0 g (0.05 mol) of dithiooxamide and a solution of pyridine (4.0 g, 0.05 mol) dissolved in methanol (100 ml). The solution was heated, with stirring, at 35° C. for 30 minutes. Ethanolamine (3.0 g, 0.05 mol) was added, and the solution was stirred and heated at 35° C. for 3 hours. The crude reaction mixture was cooled to room temperature. The acidity of this mixture was adjusted to a pH of about 2 by the addition of 37% HCl (aqueous). The methanol was removed in vacuo, and 100 ml of methylene chloride was added. The resultant mixture was stirred at room temperature for 30 minutes. Unreacted dithiooxamide (3 g) was removed as a dark brown solid by filtration of the mixture.

The filtrate was collected and the solvent was removed in vacuo. Octanoyl chloride (8.0 g, 0.05 mol) was added to the resultant oil. The reaction mixture was heated at 60° C. for 1 hour, cooled to room temperature, and 100 ml of a 50:50 mixture of methanol and water was added. Sodium bicarbonate was then added until the solution pH was about 7. The mixture was then filtered, affording 4.5 g of N,N'-di(2-octanoyloxyethyl)-dithiooxamide. The filtrate from this step was extracted with methylene chloride (2×50 ml), transferred to a round-bottomed flask and dried over magnesium sulfate. Solvent was removed at reduced pressure, affording 7.0 g (50%) of N-(2-octanoyloxyethyl)dithiooxamide as a dark black oil. The material was 80% pure as determined by gas chromatography. This corresponded to an overall yield of about 35% of pure monosubstituted material.

EXPERIMENT 4

Preparation of
N-(2-Octanoylamidoethyl)dithiooxamide

For the synthesis of the above-identified dithiooxamide, 2-octanoylamidoethylamine was needed. The amine was prepared as described in Japan Patent 67: 15,925, incorporated herein by reference. In sum, into a 250 ml round-bottomed flask, equipped with a condenser, magnetic stirrer, and heating mantle, were placed 100 g (0.82 mol) of octanenitrile, 50 g (0.82 mol) of ethylenediamine, 0.4 g of sulfur, and 20 g of water. The mixture was heated at reflux for 20 hours, and then allowed to cool to room temperature. The condenser was removed, replaced by a distillation head, and 1.0 g (0.015 mol) of powdered zinc was added. Water and ethylenediamine were removed in vacuo and the product was distilled to afford 124 g (81%) of 2-octanoylamidoethylamine; bp 155°-157° C. (0.25 mm Hg). The material partially solidified upon standing. The compound was identified by NMR spectroscopy.

The 2-octanoylamidoethylamine was used as the reactive amine to prepare N-(2-octanoylamidoethyl)dithiooxamide in the following manner. Into a 100 ml round-bottomed flask, equipped with rotary stirrer, condenser, and heating bath, were placed 2.4 g (0.02 mol) of dithiooxamide, 1.8 g (0.02 mol) of aniline, and 40 ml of methanol. The mixture was heated at 35° C for 30 minutes. To this solution, 3.8 g (0.02 mol) of 2-octanoylamidoethylamine, prepared as described above, was added, and the reaction mixture was maintained at 35° C. for 3 hours. The crude reaction mixture was cooled to room temperature, and the acidity was adjusted to a pH of about 2 by the addition of 37% HCl. A white solid precipitated, identified as an imidazoline, and was collected by filtration. Water (40 ml) was added to the filtrate to precipitate the product as a brown solid. Stirring for 30 minutes was followed by filtration and drying to afford 1.8 g (31%) of N-(2-octanoylamidoethyl)-dithiooxamide. Analysis by thin layer chromatography verified that the product was relatively pure and contained virtually no disubstituted product.

EXPERIMENT 5

Preparation of
N-(6-Propanoylamidohexyl)dithiooxamide with Auxiliary Base 1-amino-6-propanoylamidohexane, the reactive amine in the formation of N-(6-propanoylamidohexyl)-dithiooxamide, was prepared in the following manner. Into a pressure reaction kettle were placed 90.90 kg ($7.8 \times 10^2$ mol) of 1,6-hexanediamine. Propionic acid (29.09 kg, $3.9 \times 10^2$ mol) was added and the reaction mixture was heated under ambient pressure at 150° C. for 6 hours. Upon cooling, a vacuum was attached and the reaction mixture was again heated. Excess 1,6-hexanediamine was distilled off between 100°-140° C. at 5 mm Hg. The amount of recovered 1,6-hexanediamine was approximately 50 kg. The condenser was maintained at 50° C. to prevent solidification of the diamine upon cooling. Continued vacuum distillation between 140°-160° C. at 0.25 mm Hg afforded 45 kg to 54 kg of 1-amino-6-propanoylamidohexane as a clear to pale yellow oil. The yield was in the range of 65–80%. This material partially solidified upon standing. The purity of 1-amino-6-propanoylamidohexane was evaluated by gas chromatography in the following manner. A small amount of the reaction product was dissolved in chloroform. The solution was injected onto a capillary DB-1 column 15 m in length, with an inside diameter of 0.25 mm and a 0.00025 mm film thickness. The initial column temperature was 75° C., which was held for 2 minutes. The temperature was then raised 15° C./minute until a temperature of 250° C. was reached. This temperature was maintained for 5 minutes. The retention time for 1-amino-6-propanoylamidohexane was 7.70 minutes and that for 1,6-dipropanoylamidohexane was 11.5 minutes. The retention time of unreacted 1,6-hexanediamine was 2.68 minutes. Integration of the gas chromatography data indicated that the following amounts of material were present: unreacted 1,6-hexanediamine (50% to 55%), 1-amino-6-propanoylamidohexane (35% to 40%), and 1,6-dipropanoylamidohexane (5% to 10%). IR and NMR ($^1H$ and $^{13}C$) spectra were in agreement with the assigned structures.

N-(6-propanoylamidohexyl)dithiooxamide was prepared according to the following procedure. Into a reaction kettle equipped with rotary stirrer, condenser, and heating bath were placed 16.36 kg ($1.4 \times 10^2$ mol) of dithiooxamide, 218 kg of methanol, and 28 kg ($3.5 \times 10^2$ mol) of aniline. (NOTE: The reaction was also carried out without the use of the auxiliary base, see Experiment 6, with similar results. However, with the use of an auxiliary base, a ratio of reactive amine to dithiooxamide may be advantageously about 1:1.) The reaction mixture was heated and maintained at a temperature of 35° C. for 30 minutes. 1-amino-6-propanoylamidohexane (16.36 kg, 95 mol) was added and the reaction mixture was maintained at a temperature of about 35° C. for 2 hours. An additional 6.19 kg (36 mol) of 1-amino-6- propanoylamidohexane was added and the reaction was allowed to continue for an additional 4 hours. The reaction mixture was cooled to 25° C. The acidity was adjusted to a pH of below about 3 by the addition of approximately 60 kg of 37% HCl (aqueous). A vacuum was attached to the kettle, heating was begun and the methanol was removed. The temperature was maintained below 40° C. throughout the vacuum distillation. Dichloromethane (181 kg) was added to the resultant oil. This was followed by the addition of 136 kg of water. The mixture was pressure filtered through a bag or Quno filter and the phases allowed to separate. Collection of the lower organic phase followed by solvent removal at reduced pressure afforded a mixture of N-(6-propanoylamidohexyl)dithiooxamide and N,N'-di(6,6'-propanoylamidohexyl)dithiooxamide.

Tributyl phosphate (18.2 kg) was added and the purity of the resultant mixture of N-(6-propanoylamidohexyl)dithooxamide and N,N'-di(6,6'-propanoylamidohexyl)dithiooxamide was evaluated by liquid chromatography in the following manner. A small amount of the reaction mixture was dissolved in spectral grade acetonitrile. A 25 μl sample was injected onto a HP 1090 liquid chromatograph with a 15 cm×4.6 mm endcapped C-8 IBM trimethylsilyl guard column. The sample was eluted with a gradient mixture of water and acetonitrile with 2 μmol of dibutylamine additive at a flow rate of 0.75 ml/min and at a temperature of 50° C. The run gradient time was 15 minutes. The gradient slope was 100% water at 0 minutes, 75% acetonitrile at 10 minutes, and 100% acetonitrile at 15 minutes. The UV detector was set at 305 nm. Dithiooxamide was found to elute at 5.5 minutes, N-(6-propanoylamidohexyl)dithiooxamide eluted at 9.5 minutes, and N,N'-di(6,6'-propanoylamidohexyl)dithiooxamide eluted at 10.9 minutes. The amount of N-(6-propanoylamidohexyl)dithiooxamide was found to be 11.1 kg (40 mol) and the amount of N,N-di(6,6'-propanoylamidohexyl)dithiooxamide was found to be 7.5 kg (17.4 mol). The mole ratio of the monosubstituted product to the disubstituted product was 2.3:1.

A sample of the reaction mixture was adsorbed onto a silica gel column and eluted with a 50:50 mixture of hexane and ethyl acetate. N-(6-propanoylamidohexyl)-dithiooxamide eluted first, followed by N,N'-di(6,6'-propanoylamidohexyl)dithiooxamide. $^{13}$C NMR spectra of the thus purified samples of both N-(6-propanoylamidohexyl)dithiooxamide (the major product) and N,N'-di(6,6'-propanoylamidohexyl)dithiooxamide (formed as the minor product) were in agreement with the assigned structures.

EXPERIMENT 6

Preparation of N-(6-Propanoylamidohexyl)dithiooxamide without Auxiliary Base

Into a 250 ml round-bottomed flask, equipped with a magnetic stirrer, condenser, and heating bath, were placed 6.0 g (0.05 mol) of dithiooxamide and 100 ml of methanol. The mixture was stirred and heated at 35° C. for 30 minutes. 1-amino-6-propanoylamidohexane (4.3 g, 0.025 mol), prepared as in Experiment 5 above, was added in one portion and the addition flask washed with methanol. The reaction mixture was stirred at 35 C. for an additional 22 hours. The crude reaction mixture was cooled to room temperature and the acidity adjusted to a pH of 2 by the addition of 37% HCl. The solvent was removed under vacuum, which was followed by the addition of 50 ml of CH$_2$Cl$_2$ and 50 ml of water. The mixture was stirred and filtered to afford 2.9 g of unreacted dithiooximide. The two layers of the mother liquor were separated and the aqueous layer was discarded. Removal of the CH$_2$Cl$_2$ at reduced pressure afforded 4.4 g of product as an oil. The ratio of N-(6-propanoylamidohexyl)dithiooxamide to N,N'-di(6,6'-propanoylamidohexyl)dithiooxamide determined as in Experiment 5 above was 2.6:1.

EXPERIMENT 7

Using the general procedure of Experiment 1 above, the following monosubstituted dithiooxamides were prepared:

N-octadecyldithiooxamide (reactive amine = octadecylamine)
N-tetradecyldithiooxamide (reactive amine = tetradecylamine)
N-hexadecyldithiooxamide (reactive amine = hexadecylamine)

The procedure outlined in Experiment 1 above may be followed in the synthesis of a variety of dithiooxamides, including the following monosubstituted dithiooxamides:

N-methyldithiooxamide (reactive amine = methylamine)
N-ethyldithiooxamide (reactive amine = ethylamine)
N-octyldithiooxamide (reactive amine = octylamine)
N-decyldithiooxamide (reactive amine = decylamine)
N-(4-methylbenzyl)dithiooxamide (reactive amine = 4-methylbenzylamine)
N-(4-dimethylaminobenzyl)dithiooxamide (reactive amine = 4-dimethylaminobenzylamine)
N-(3,4-dichlorobenzyl)dithiooxamide (reactive amine = 3,4-dichlorobenzylamine)
N-cyclopropyldithiooxamide (reactive amine = cyclopropylamine)
N-(11-carboxydecyl)dithiooxamide (reactive amine = 11-carboxydecylamine)
N-(3-diethylaminopropyl)dithiooxamide (reactive amine = 3-diethylaminopropylamine)
N-benzyldithiooxamide (reactive amine = benzylamine)
N-(4-chlorobenzyl)dithiooxamide (reactive amine = 4-chlorobenzylamine)
N-(4-methoxybenzyl)dithiooxamide (reactive amine = 4-methoxybenzylamine)
N-butyldithiooxamide (reactive amine = butylamine)
N-(2-phenylethyl)dithiooxamide (reactive amine = 2-phenylethylamine)
N-(1-naphthylmethyl)dithiooxamide (reactive amine = 1-naphthylmethylamine)
N-(1-methyl-2-phenoxyethyl)dithiooxamide (reactive amine = 1-methyl-2-phenoxyethylamine)
N-(3-ethoxypropyl)dithiooxamide (reactive amine = 3-ethoxypropylamine)
N-alkoxypropyldithiooxamide (mixture, C$_8$–C$_{10}$ alkyl) (reactive amine = mixture of C$_8$–C$_{10}$ alkoxypropylamines)
N-alkoxypropyldithiooxamide (mixture, C$_{12}$–C$_{15}$ alkyl) (reactive amine = mixture of C$_{12}$–C$_{15}$ alkoxypropylamines)

Using the general procedure outlined in Experiment 3, N-(2-dodecanoyloxyethyl)dithiooxamide was synthesized from N-(2-hydroxyethyl)dithiooxamide and dodecanoyl chloride, and N-(2-decanoyloxyethyl)dithiooxamide was synthesized from N-(2-hydroxyethyl)dithiooxamide and decanoyl chloride.

Using the general procedure outlined in Experiments 4, 5, and 6 above, the following list of monosubstituted dithiooxamides were prepared. In some instances, improvement in isolation of the product was achieved with the use of the auxiliary base present in an amount, relative to dithiooxamide, toward the lower end of the most preferred range of 0.5 to 1.2 molar equivalents. That is, initially, using about 0.5 to 0.8 molar equivalents of auxiliary base relative to dithiooxamide produces advantageous results for certain of the following compounds.

N-(2-hexanoylamidoethyl)dithiooxamide (reactive amine = 2-hexanoylamidoethylamine)

N-(2-acetamidoethyl)dithiooxamide (reactive amine = 2-acetamidoethylamine)

N-(6-phenylacetamidohexyl)dithiooxamide (reactive amine = 1-amino-6-phenylacetamidohexane)

N-(12-propanoylamidododecyl)dithiooxamide (reactive amine = 1-amino-12-propanoylamidododecane)

N-(12-octanoylamidododecyl)dithiooxamide (reactive amine = 1-amino-12-octanoylamidododecane)

N-(2-phenylacetamidoethyl)dithiooxamide (reactive amine = 2-phenylacetamidoethylamine)

N-(6-butanoylamidohexyl)dithiooxamide (reactive amine = 1-amino-6-butanoylamidohexane)

N-(6-octanoylamidohexyl)dithiooxamide (reactive amine = 1-amino-6-octanoylamidohexane)

N-(6-undecanoylamidohexyl)dithiooxamide (reactive amine = 1-amino-6-undecanoylamidohexane)

N-(5-propanoylamido-2-methylpentyl)dithiooxamide mixed with N-(5-propanoylamido-4-methylpentyl)dithiooxamide* (reactive amine = mixture of 1-amino-2-methyl-5-propanoylamidopentane and 1-amino-4-methyl-5-propanoylamidopentane)

N-(5-pentanoylamido-2-methylpentyl)dithiooxamide mixed with N-(5-pentanoylamido-4-methylpentyl)dithiooxamide* (reactive amine = mixture of 1-amino-2-methyl-5-pentanoylamidopentane and 1-amino-4-methyl-5-pentanoylamidopentane)

N-(5-octanoylamido-2-methylpentyl)dithiooxamide mixed with N-(5-octanoylamido-4-methylpentyl)dithiooxamide* (reactive amine = mixture of 1-amino-2-methyl-5-octanoylamidopentane and 1-amino-4-methyl-5-octanoylamidopentane)

N-(5-heptanoylamido-2-methylpentyl)dithiooxamide mixed with N-(5-heptanoylamido-4-methylpentyl)dithiooxamide* (reactive amine = mixture of 1-amino-2-methyl-5-heptanoylamidopentane and 1-amino-4-methyl-5-heptanoylamidopentane)

N-(5-nonanoylamido-2-methylpentyl)dithiooxamide mixed with N-(5-nonanoylamido-4-methylpentyl)dithiooxamide* (reactive amine = mixture of 1-amino-2-methyl-5-nonanoylamidopentane and 1-amino-4-methyl-5-nonanoylamidopentane)

*NOTE: These dithiooxamides are all mixtures of the 2-methylpentyl and the 4-methylpentyl products because the diamine used in the formation of the reactive amine was 1,5-diamino-2-methylpentane. In the reaction between this diamine and the appropriate carboxylic acid, reaction between the amine group at the "1" position and the acid resulted in formation of the 4-methylpentyl product upon subsequent reaction with dithiooxamide. Similarly, the reaction of the amine group at the "5" position with the acid resulted in formation of the 2-methylpentyl product upon further reaction with dithiooxamide. Furthermore, each of the 2-methylpentyl and 4-methylpentyl dithiooxamide products contains a chiral center, so each of these dithiooxamides is actually a mixture of 2 optical isomers.

The invention has been described with reference to various specific and preferred embodiments and techniques. It should be understood, however, that many variations and modifications may be made while remaining within the spirit and scope of the invention.

What is claimed and desired to be secured by Letters Patent is as follows:

1. A method for the preparation of an N-(monosubstituted dithiooxamide compound from the reaction of dithiooxamide and a reactive amine; said method including the steps of:
   (a) conducting the reaction in a solution containing an organic solvent and in the absence of aqueous hydroxide ion;
   (b) providing an initial concentration of dithiooxamide in the solution of no greater than about 15% by weight;
   (c) providing an initial concentration of the reactive amine in the solution of no greater than about 15% by weight;
   (d) providing an initial molar ratio of dithiooxamide to reactive amine in the solution within the range of about 0.8:1 to 3:1; and,
   (e) conducting the reaction for a sufficient period of time to achieve a molar ratio of N-(monosubstituted)dithiooxamide product to N,N'-(disubstituted)dithiooxamide product of greater than 1:1.

2. The method according to claim 1 wherein the initial concentrations of the reactive amine and dithiooxamide in the solution are provided such that each is initially no greater than about 10% by weight.

3. The method according to claim 2 further comprising a step of:
   (a) quenching the reaction of dithiooxamide and reactive amine by adding an effective amount of an acid to the solution.

4. The method according to claim 1 including a step of providing an amount of auxiliary nitrogen base in the solution effective to generate a greater molar ratio of N-(monosubstituted) dithiooxamide compound to N,N'-(disubstituted)dithiooxamide compound than would be obtained in the absence of the auxiliary nitrogen base.

5. The method according to claim 4 further comprising a step of:
   (a) quenching the reaction of dithiooxamide and reactive amine by adding an effective amount of an acid to the solution.

6. The method according to claim 5 further comprising a step of:
   (a) maintaining a temperature of the solution within the range of about 30° C. to 40° C. during the reaction.

7. The method according to claim 4 wherein step of providing a nitrogen base includes a step of providing about 0.5 to 3.0 molar equivalents of the auxiliary nitrogen base in the solution, relative to the initial amount of dithiooxamide.

8. The method according to claim 7 wherein the step of providing a nitrogen base includes a step of providing about 0.5 to 1.2 molar equivalents of the auxiliary nitrogen base in the solution, relative to the initial amount of dithiooxamide.

9. The method according to claim 4 wherein the auxiliary nitrogen base is selected from the group consisting of pyridine, aniline, diethylamine, and mixtures thereof.

10. The method according to claim 1 further comprising a step of:
    (a) quenching the reaction of dithiooxamide and reactive amine by adding an effective amount of an acid to the solution.

11. The method according to claim 10 further comprising a step of:

(a) maintaining a temperature of the solution within the range of about 30° C. to 40° C. during the reaction.

12. The method according to claim 10 wherein the step of quenching includes adding a strong mineral acid.

13. The method according to claim 10 wherein the step of quenching includes adding HCl.

14. The method according to claim 10 wherein the step of quenching the reaction by adding acid includes a step of adding the acid to the solution in an amount effective to render a pH within the range of about 2 to 5.

15. A method according to claim 1 wherein said step of conducting the reaction for a sufficient period of time to achieve a molar ratio of N-(monosubstituted)dithiooxamide product to N,N'-(disubstituted)dithiooxamide product of greater than 1:1 includes conducting the reaction for sufficient time to achieve at least a 32% yield of N-(monosubstituted)dithiooxamide product, based on an initial presence of whichever of reactive amine and dithiooxamide starting material is limiting.

16. The method according to claim 15 including a step of providing an amount of auxiliary nitrogen base in the solution effective to generate a greater molar ratio of N-(monosubstituted) dithiooxamide compound to N,N'-(disubstituted)dithiooxamide compound than would be obtained in the absence of the auxiliary nitrogen base.

17. The method according to claim 16 wherein the step of providing a nitrogen base includes a step of providing about 0.5 to 1.2 molar equivalents of the auxiliary nitrogen base in the solution, relative to an initial amount of dithiooxamide present.

18. The method according to claim 16 wherein the auxiliary nitrogen base is selected from the group consisting of pyridine, aniline, diethylamine, and mixtures thereof.

19. The method according to claim 16 further comprising a step of:
(a) quenching the reaction of dithiooxamide and reactive amine by adding an effective amount of an acid to the solution.

20. The method according to claim 16 further comprising a step of:
(a) maintaining a temperature of the solution within a range of about 30° C. to 40° C. during the reaction.

21. A method for the improved preparation of an N-(monosubstituted)dithiooxamide compound from the reaction of dithiooxamide and a reactive amine; said method comprising the steps of:
(a) conducting the reaction in a solution; and
(b) providing an amount of an auxiliary nitrogen base in the solution effective to generate a greater ratio of N-(monosubstituted)dithiooxamide compound to N,N'-(disubstituted) dithiooxamide compound, than would be obtained in the absence of the auxiliary nitrogen base.

22. The method according to claim 21 wherein said nitrogen base is selected from the group consisting of: aromatic primary amines; secondary aliphatic amines; tertiary aliphatic amines; aromatic nitrogen-containing heterocycles; and mixtures thereof.

23. The method according to claim 21 wherein said auxiliary nitrogen base is selected from the group consisting of aniline, pyridine, diethylamine, and mixtures thereof.

* * * * *